US00PP22250P2

(12) United States Plant Patent
Hurd

(10) Patent No.: US PP22,250 P2
(45) Date of Patent: Nov. 15, 2011

(54) ***HIBISCUS* PLANT NAMED 'PARTY FAVOR'**

(50) Latin Name: ***Hibiscus* hybrid (L.)**
Varietal Denomination: Party Favor

(75) Inventor: Kevin A. Hurd, Grand Rapids, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 12/804,404

(22) Filed: Jul. 21, 2010

(51) Int. Cl.
*A01H 5/00* (2006.01)

(52) U.S. Cl. ..... Plt./257

(58) Field of Classification Search ..... Plt./257
See application file for complete search history.

*Primary Examiner* — Kent L Bell

(57) ABSTRACT

The new and distinct plant cultivar of hardy *Hibiscus* named 'Party Favor' comprising a multitude of flowers with ruffled and heavily overlapped cotton-candy pink petals and deep magenta eye, three to five-lobed maple-like foliage with purple tinting and heavily branched stems heavily with purple tinting producing a numerous flowers over at least 12 weeks during the summer and early fall until frost.

1 Drawing Sheet

Botanical classification: *Hibiscus* hybrid (L.).
Variety denomination: 'Party Favor'.

BACKGROUND AND ORIGIN OF THE PLANT

The present invention relates to the new and distinct hardy *hibiscus* plant, *Hibiscus* 'Party Favor' hybridized by Kevin A. Hurd in the summer of 2006 at a nursery in Zeeland, Mich. The new Plant, originally assigned the breeder identification number 06-10-04 is a cross between *Hibiscus* 'Fantasia' U.S. Plant Pat. No. 11,853 as the female parent (pod parent) times *Hibiscus* 'Fireball' U.S. Plant Pat. No. 13,634 as the male parent (pollen parent). *Hibiscus* 'Party-Favor' has been asexually propagated both by shoot tip stem cuttings and sterile tissue culture at the same nursery in Zeeland, Mich. first since 2008. The resultant plants have been found to be stable and true to type in successive generations of asexual reproduction.

SUMMARY OF THE PLANT

*Hibiscus* 'Party Favor' differs from its parents as well as all other hardy *hibiscus* known to the applicant in many traits. The flower of 'Party Favor' is more ruffled producing heavier substance petals that hold up to wind and rain better than either parent. The flower color of 'Party Favor' is a cotton-candy pink with a deep magenta eye whereas 'Fireball' flower is red with a red eye nearly identical in color to the petal and 'Fantasia' is lavender pink with a fuchsia eye. Flower size of 'Party Favor' is intermediate between the two parents, much larger than 'Fantasia' but not quite as large as 'Fireball'. The petals of 'Party Favor' overlap much more than 'Fireball' and are similar to the overlap of 'Fantasia'. The flower color of 'Party Favor' is cotton-candy pink with a deep magenta eye compared to the red flower of 'Fireball' or the lavender pink flower of 'Fantasia'. The flower shape is flatter than 'Fantasia' with more ruffling in the petals than either 'Fantasia' or 'Fireball'. The foliage shape of 'Party Favor' is variable, but in general is as dissected as 'Fireball' and more dissected than 'Fantasia'. The most similar *hibiscus* to 'Party Favor' are *Hibiscus* 'Pink Elephant' (U.S. Plant Pat. No. 21,883) and 'Anne Arundel' (not patented). The new plant has more ruffling, heavier substance petals and much greater petal overlap than both 'Pink Elephant' and 'Anne Arundel'. The foliage has more purple pigment than 'Pink Elephant' or 'Anne Arundel' and is more dissected than 'Pink Elephant'. The new plant is also shorter than both 'Pink Elephant' or 'Anne Arundel'. The new plant differs from 'Sultry Kiss' (co-pending application Ser. No. 12/804,429) in that 'Party Favor' has a cotton-candy pink based petal with a deeper magenta eye, is taller, and the flower slightly smaller.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

GENERAL DESCRIPTION OF THE PLANT

Figure 1:
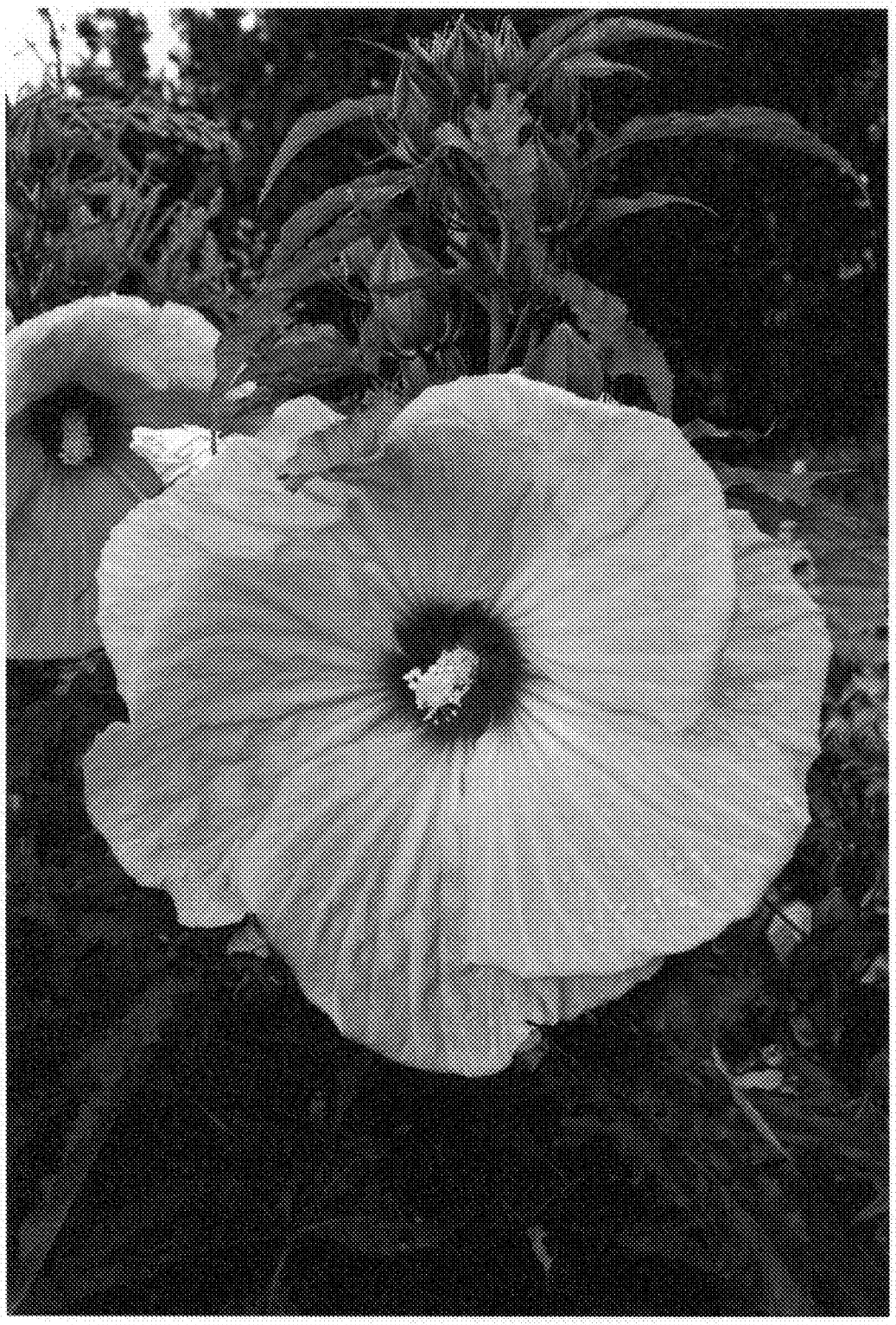
FIG. 1 shows the new plant in flower during the early part of the flowering season.

*Hibiscus* 'Party Favor' is distinct from all other *Hibiscus* known to the applicant in the following combined traits:

1. Ruffled and heavily overlapped cotton-candy pink petals with deep magenta eye.
2. Three to five-lobed maple-like foliage with purple tinting.
3. Stems heavily branched with purple tinting.

DETAILED BOTANICAL DESCRIPTION

The following descriptions and color references are based on The 2001 edition of The Royal Horticultural Society Colour Chart except where common dictionary terms are used. The new plant, *Hibiscus* 'Party Favor', has not been observed under all possible environments. The phenotype may vary slightly with different environmental conditions, such as temperature, light, fertility, moisture and maturity levels, but without any change in the genotype. The following observations and size descriptions are of two-year old and three-year old plants in the trial field of a nursery in Zeeland, Mich. with supplemental fertilizer and water as needed. The plants were not treated with plant grow regulators.

Botanical classification: *Hibiscus* L.xhybrid.

Parentage: *Hibiscus* 'Fantasia' U.S. Plant Pat. No. 11,853 (female) times *Hibiscus* 'Fireball' U.S. Plant Pat. No. 13,634 (male);

Parentage: *Hibiscus* 'Fantasia' U.S. Plant Pat. No. 11,853 (female) times *Hibiscus* 'Fireball' U.S. Plant Pat. No. 13,634 (male);

Propagation:

*Method.*—Stem cuttings and sterile laboratory tissue culture division.

*Time to initiate roots from tissue culture.*—About two weeks.

*Rooting habit.*—Normal, thick to about 3.5 cm diameter, fleshy, branching; root color creamy white depending on soil type.

*Crop time.*—Under normal summer growing conditions 12 to 16 weeks to flower in a four-liter container from cutting. Plant vigor is very good.

Plant description:

*Plant shape and habit.*—Hardy herbaceous perennial with 7 to 14 thick upright branched main stems producing upright rounded mound; 20 to 28 branches per main stem protruding at 45° to 60° angle from vertical.

*Plant size.*—Unpinched plant with stems 120 to 150 cm tall, average about 135 cm tall from soil line; overall plant 120 to 150 cm wide at the widest point; stem width 2.5 to 3.5 cm at base.

*Internode length.*—Unpinched plant varied between 3.5 to 7.0 cm, average about 4.5 cm.

*Foliage description.*—Opposite; dentate; glabrous (top and bottom); irregularly cleft palmate with lobes cleft over half way to base to nearly all the way to base; texture dull above and below; palmately veined; 20 to 34 cm across and 12 to 22 cm long, average 22 cm wide and 19 cm long.

*Foliage color.*—Adaxial nearest RHS 143A with purple tinting through mid-season in an irregular blotchy pattern of RHS 187A and palmate veins nearest RHS 187D; abaxial nearest RHS 138A with veins nearest RHS 145C having slight tinting of RHS 187B.

*Petioles.*—3.5 to 13 cm long and 4 to 6 mm wide at base; proximally more piano-convex with the top portion flattened and distally more cylindrical; above RHS 144A with tinting between RHS 178D and RHS 181A, below nearest RIIS N144A with stipling of nearest RHS 182B.

Flower description:

*Flowers.*—Solitary, flat, upward and outwardly facing; 20 to 22 cm across, petals opening nearly flat to 3.0 cm deep without column, smaller later in flowering season; persist for a one to two days; effective for at least 12 weeks beginning mid to late July and lasting into October; no detectable fragrance.

*Buds one day prior to opening with showing petals.*—About 8.0 cm long and 4.5 cm in diameter, muticous apex and bluntly rounded base, unopened petals wrinkled at veins, petal color nearest RHS 73D; prior to showing petals buds are ovoid, about 3.5 cm long and 2.5 cm in diameter, with acute apex; ridged along sepal joints; color nearest RHS 144A with rare accent tinting of nearest RHS 183D.

*Epicalyx.*—Entire, smooth, glabrous, linear with sharply acute apex, curved around sepals; 10 to 12 per flower; about 2.5 cm long tapering to base of 3 mm wide; color RHS 144A on inner and RHS 144C on outer surface with occasional tinting of tips nearest RHS 183D.

*Sepals.*—Five, proximal half connate forming campanulate star-shaped calyx; acute apex; about 3.8 cm long and 2.0 cm wide; outer color nearest RHS 144A with occasional tinting of RHS 183D and inner color nearest RHS 144C; three primary sepal veins nearest the same color as the surrounding sepal tissue on inside and outside.

*Petals.*—Five; adnate to stamen column at base, overlapping to nearly 100% at widest part of petal (each petal nearly being overlapped by the other two petals on either side); 12.0 to 13.0 cm long and 15.0 to 17.5 cm wide at widest portion; front petal color ranging between lighter than RHS N57D and between RHS 64C and RHS 64D with a shiny 5.0 cm wide eye of nearest RHS 53A with a 0.5 cm long jetting streaks of nearest RHS 60C as it feathers into petal base color, back petal color nearest RHS 62C; veins palmate, nearest RHS 62D on back and nearest RHS 73D to the same as the main petal color on petal front.

*Gynoecium.*—Style: enclosed in column.

*Column.*—7.0 to 9.0 cm long and 1.5 cm wide at base; column color nearest RHS 19C with a slight amount of tinting nearest RHS 63D.

*Style.*—Split into five branches in the distal 7 to 10 mm; nearest RHS N155C.

*Androccium.*—Filaments: numerous, about 120; less than 1 mm in diameter and about 7 mm long; attached to nearly the entire length of column; nearest RHS 155D. Anthers: reniform; about 2 mm long and 1 mm wide; nearest RHS11D.

*Pollen.*—Numerous, globose, less than 0.1 mm long; between RHS 18C and RHS 18B.

*Pedicel.*—Minutely pubescent; length from base of sepal to abscission point about 2.0 cm long and 4 mm wide on early flowers; flowers are held out easily visible by up to 7.0 cm long from abscission point to stem and 4 mm wide on early flowers shortening to about 3.0 cm distally on stem; color nearest RHS 138A.

*Peduncle.*—Branched scape; glabrous, rounded; average 135 cm tall; 15 to 26 flowers per apical scape without pinching; branched with 20 to 28 branches per main stem; axillary branches having 1 to 7 flowers; average about 65 flowers per stem; color nearest RHS 153C with tinting of nearest RHS 53B.

Fruit: Loculicidal capsule; glabrous; globose, occasionally with abruptly acute apex; mature color RHS N199B;

Seed: Minutely floccose, globose to slightly reniform; 3 to 4 mm in diameter; RHS 200A;

Disease resistance: Resistance beyond that of other hardy *hibiscus* cultivars has not been observed. The plant grows best with warm temperatures, plenty of moisture and adequate drainage, but is able to tolerate some drought when mature. Hardiness at least from USDA zone 4 through 9, and other disease resistance is typical of that of other *hibiscus* cultivars.

I claim:

1. A new and distinct cultivar of hardy hybrid *Hibiscus* plant named 'Party Favor' as herein described and illustrated, with ruffled and heavily overlapped cotton-candy pink petals and deep magenta eye, three to five-lobed maple-like foliage with purple tinting and heavily branched stems heavily with purple tinting producing a multitude of flowers over at least 12 weeks during the summer and early fall until frost, and suitable as a potted plant, for the garden, and for cut flower arrangements.

* * * * *